United States Patent [19]

Blommaert

[11] Patent Number: 4,633,708

[45] Date of Patent: Jan. 6, 1987

[54] CONSISTOMETER CONTAINER FOR TESTING RHEOLOGICALLY EVOLUTIVE MATERIAL

[75] Inventor: Paul A. G. Blommaert, Tournai, Belgium

[73] Assignee: Total Compagnie Francaise des Petroles, Paris, France

[21] Appl. No.: 766,374

[22] Filed: Aug. 16, 1985

[30] Foreign Application Priority Data

Aug. 31, 1984 [FR] France .................................. 84 13538

[51] Int. Cl.$^4$ ............................................. G01N 11/14
[52] U.S. Cl. ........................................ 73/59; 220/4 E; 220/DIG. 25
[58] Field of Search ...................... 73/59, 60; 220/4 E, 220/5 R, DIG. 25, 4 B, 319; 285/419, 373

[56] References Cited

U.S. PATENT DOCUMENTS

| | | | |
|---|---|---|---|
| D. 231,367 | 4/1974 | Willinger et al. | 220/4 E X |
| 625,448 | 5/1899 | Jaenichen | 285/373 X |
| 733,995 | 7/1903 | Profitlich et al. | 285/373 |
| 3,435,666 | 4/1969 | Fann | 73/59 X |
| 4,014,393 | 3/1977 | Hensel, Jr. | 220/4 E X |
| 4,103,943 | 8/1978 | Curtin | 285/419 |
| 4,466,276 | 8/1984 | Ruyak et al. | 73/59 |
| 4,524,611 | 6/1985 | Richon et al. | 73/59 |
| 4,534,209 | 8/1985 | Sanders | 73/59 |

Primary Examiner—Stewart J. Levy
Assistant Examiner—Joseph W. Roskos
Attorney, Agent, or Firm—Sughrue, Mion, Zinn, Macpeak and Seas

[57] ABSTRACT

A consistometer container for testing rheologically evolutive materials is generally cylindrical or frustoconical in shape, and has a side wall composed of two half-shells 20, 21 which are connected together along two generatrices 40, 41 and which have externally threaded longitudinal end portions 26, 27. Two clamp rings 22, 23, are threaded onto the side wall ends to clamp the half-shells together. Such a construction enables the testing of a progressively hardening material without having to separate the material from the container as soon as the tests are finished.

3 Claims, 8 Drawing Figures

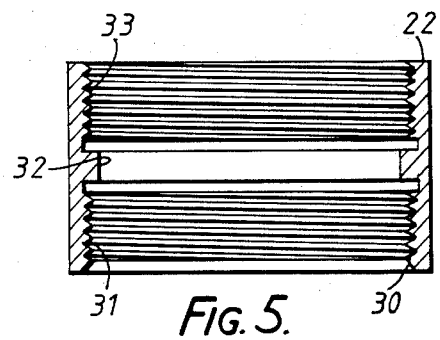
FIG. 5.
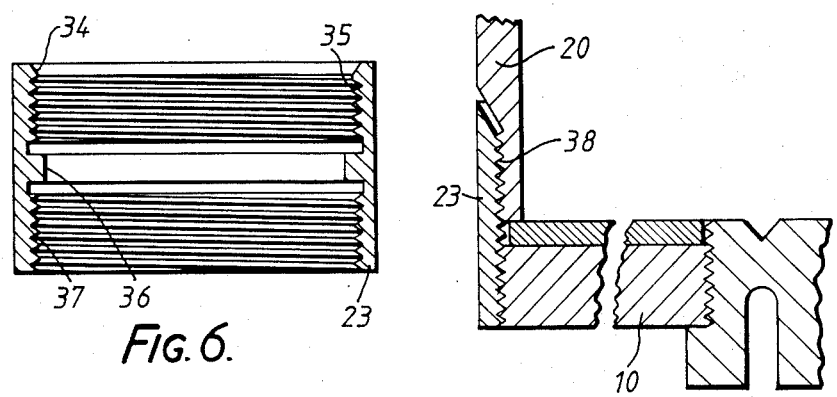
FIG. 6.
FIG. 7.
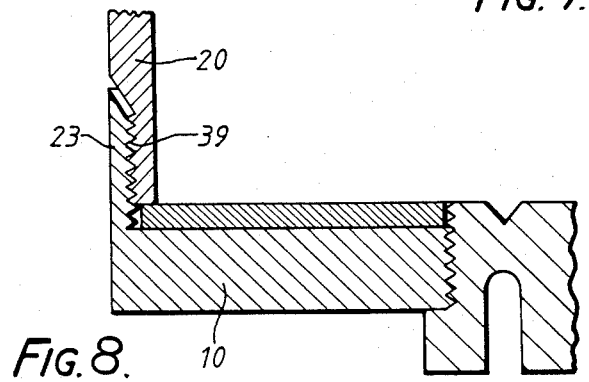
FIG. 8.

CONSISTOMETER CONTAINER FOR TESTING RHEOLOGICALLY EVOLUTIVE MATERIAL

BACKGROUND OF THE INVENTION

The invention relates to a container for receiving a rheologically evolutive material for use in a consistometer and cooperating therein with measuring equipment permitting the study of the rheological evolution of this material.

The material being studied may in particular be a cement of the inorganic, organic or mixed type.

A consistometer of this kind makes it possible to follow the evolution in time of the rheological process of a progessively hardening material under conditions very close to the real conditions for which it is desired to gain knowledge of this evolution. In the construction industry, this will apply to concretes, mortars or grouts carried in rotary-container vehicles, and, in drilling, to cement grouts injected into wells.

Although the invention is not restricted to this last-mentioned application, it will be described more particularly in the case of drilling cements, because in this application experimentation conditions are particularly difficult.

In wells, particularly petroleum wells, it is necessary to pump a liquid cement in order to inject it between a metal casing and the ground formation bordering the borehole. The setting of the liquid cement isolates the various layers of the ground formation around the borehole and holds the casing in place.

For successful cementing it is important to use a liquid cement having a clearly determined pumpability time (or setting time). Too short a time would result in premature clogging, and too long a time would needlessly delay resumption of work after cementing.

A test for determining pumpability time generally takes several hours and sometimes takes up an entire working day. As it is desired to recover the cement slurry test container, an operator must be present at the end of the test in order to be able to separate the cement undergoing setting from the container holding it, before the cement hardens completely. This results in considerable problems in the organization of the work, and in sometimes the termination of a test before it has been possible to reach the maximum consistency value compatible with pumping.

It has already been proposed to make in situ measurements of rheological properties of a fluid by means of a measuring apparatus having an external cylindrical container composed of two halves capable of being joined together for use and of being separated for cleaning, the test involving rotation of shafts carrying these two halves. This system is cumbersome and would not be suitable for a consistometer in which the container receiving the material to be analysed must be placed in a chamber in which pressure and/or temperature is or are controllable. It would be even less suitable for a consistometer in which the container must itself be rotated.

SUMMARY OF THE INVENTION

According to the invention there is provided a container for rheologically evolutive materials, and for mounting in a consistometer and cooperating therein with measuring equipment for making an analysis of rheological evolution, comprising side walls of generally cylindrical or frustoconical shape and comprising two longitudinal half-shells (20,21) adapted to be connected to one another along two diametrically opposite generatrices, and having externally threaded longituindal end portions and two clamp rings for screwing respectively one on each of the threaded longitudinal end portions to clamp the two half-shells one against the other.

Preferably the half-shells have a continuous inner face of semicylindrical or semifrustoconical shape and an outer face comprising a semicylindrical or semifrustoconical main central portion lying between two externally threaded end portions of smaller diameter and connected to the central portion face by chamfers, and each of the clamp rings has a frustoconical annular face whose inclination is complementary to that of the respective chamfer and which is intended to be applied against the respective one of the chamfers on threading of the clamp rings on the half-shells.

The half-shells preferably penetrate one into the other along their connecting generatrices. This penetration is preferably achieved with the aid of complementary longitudinal surfaces having a V-shaped cross-section.

BRIEF DESCRIPTION OF THE DRAWINGS

Embodiments according to the invention will now be described, by way of example only, with reference to the accompanying drawings.

In the drawings:

FIG. 5 is a vertical section through an upper clamp ring forming part of the cylindrical side wall of the container of FIG. 3;

FIG. 6 is a vertical section of a lower clamp ring forming part of the cylindrical side wall of the container of FIG. 3; and FIGS. 7 and 8 are vertical half-sections of modified lower clamp rings.

DETAILED DESCRIPTION OF THE PREFERRED EMBODIMENTS

Figure 1:
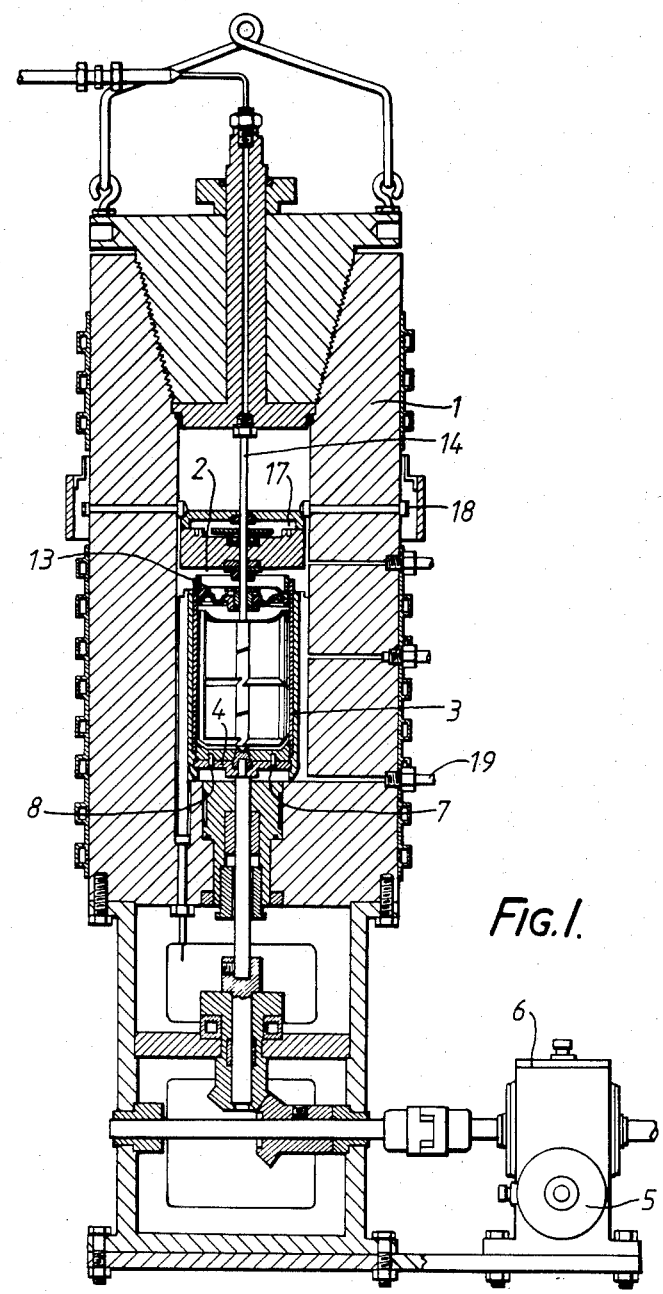
FIG. 1 is a partial vertical section of a consistometer assembly.

FIG. 1 shows a complete consistometer comprising a vessel 1 of great thickness, inside which is formed a chamber 2 in which is placed a generally cylindrical container 3 for receiving a material whose rheology it is desired to study. The container 3 rests on a turntable 4 driven rotationally by a motor 5 via a reduction transmission 6. The container 3 is held relative to the turntable for rotation therewith by two pins 7 and 8, which can be seen more clearly in FIG. 2, and which penetrate into corresponding sockets provided in the turntable 4.

Figures 2, 3:
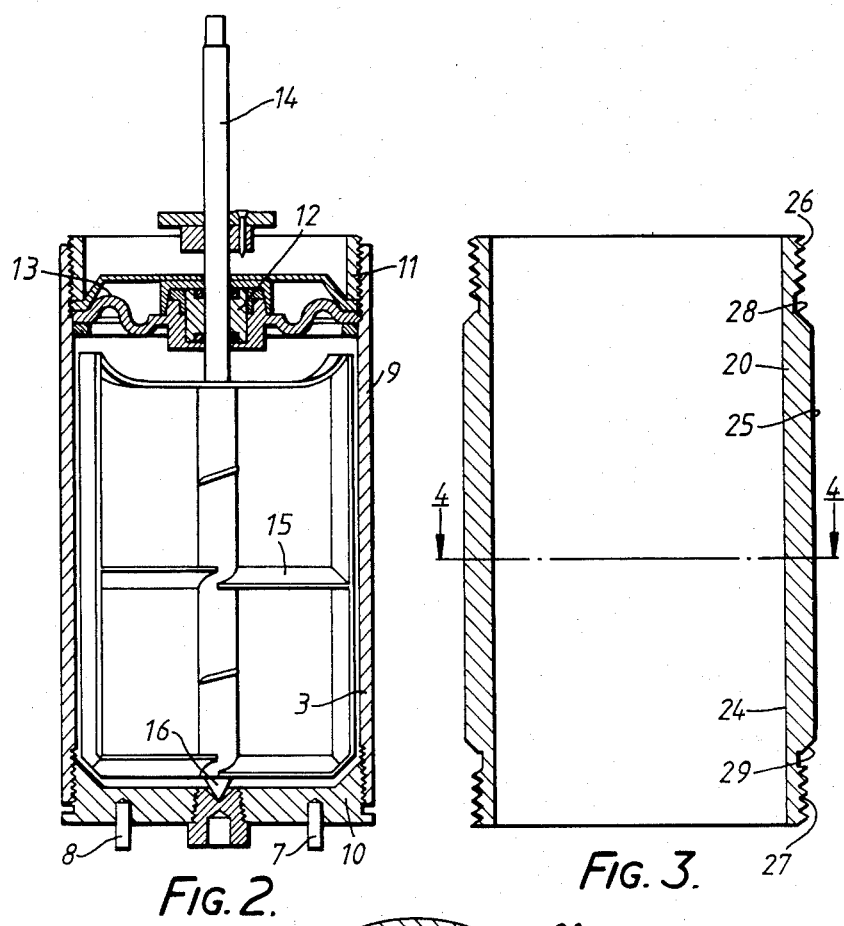
FIG. 2 is a vertical section on a larger scale of the container used in the consistometer of FIG. 1.
FIG. 3 is a vertical section through part of the side wall of a consistometer container in accordance with the invention, the wall being as shown cylindrical.

The container 3, which is shown in FIG. 2, comprises a vertical cylindrical side wall 9, to the lower end of which a base 10, carrying the pins 7 and 8, is screwed, and to the upper end of which is screwed a ring 11 retaining an assembly comprising a leaktight central bearing 12 and a deformable diaphragm 13 which are such that a shaft 14 carrying a bladed agitator 15 can pass sealingly through the top of the container 3 and the pressure in the chamber 2 is communicated to the interior of the container 3 by deformation of the diaphragm 13. The bladed agitator 15, which is not rotationally fixed to the container 3, is supported on the base 10 by a pivot 16.

Returning to FIG. 1, above the container 3 there is a measuring unit 17, of which not all the details are shown and which comprises, in conventional manner, a spiral spring tending to oppose the rotation of the shaft 14 and a blade fastened to the shaft and adapted to be displaced over a potentiometer resistor which is connected to the outside by conductors 18.

The chamber 2 receives pressurized oil through a pipe 19 and the oil is brought to the desired temperature by an electric heater. It is thus possible to establish in the chamber 2, and consequently in the container 3, conditions of temperature and pressure close to those existing in wells where cementing is required.

It is desired to facilitate the separation of the hardened liquid cement from the container 3 and thus to be able, without risk of ruining the container and its accessories, to allow the consistometer to operate without supervision and to stop automatically as soon as the voltage, shown on the potentiometer, has reached the value corresponding to the maximum consistency of cement permissible for the pumpability of the cement. For this purpose, instead of making the cylindrical side wall 9 in one piece, in accordance with the invention it is made of four parts comprising two half-shells 20 and 21, shown in FIG. 4, an upper clamp ring 22, shown in FIG. 5, and a lower clamp ring 23, shown in FIG. 6.

The half-shells 20 and 21 each have a semicylindrical inner face 24 which is continuous over their entire height, while each outer face comprises a semicylindrical main central portion 25 and two externally threaded end portions being an upper portion 26 and lower portion 27, of smaller diameter than the central portion. The connection between these portions is made by an upper semicircular chamfer 28 and a lower semicircular chamfer 29.

The upper ring 22 comprises from bottom to top: a frustoconical face 30 which is applied against the chamfer 28 of the half-shells 20 and 21 and clamps them against one another; an inner threaded portion 31 for engaging the upper external threaded portion 26 of the half-shells 20 and 21; an internal annular shoulder 32; and a threaded portion 33. The shoulder 32 and threaded portion 33 are intended to receive the assembly comprising the bearing 12, the diaphragm 13, and the ring 11.

The lower ring 23 comprises from top to bottom: a frustoconical face 34 which is applied against the chamfer 29 of the half-shells 20 and 21 and clamps them against one another; an internal threaded portion 35 for engaging the bottom external threaded portion 27 of the half-shells 20 and 21; an internal annular shoulder 36; and an internal threaded portion 37. The shoulder 36 and threaded portion 37 are intended to receive the base 10.

FIGS. 7 and 8 show modifications of the bottom ring 23, in which the shoulder 36 is omitted. In the modification of FIG. 7, one and the same threaded portion 38 serves in its upper portion, by engaging with the lower threaded portions of the half-shells 20 and 21, to hold the half-shells against one another, and, in its lower portion, to engage the base 10. The threaded portion 38 therefore serves the functions of both the threaded portions 35 and 37. In the modification of FIG. 8, the ring 23 is made integral with or fixed to the base 10 and a single screwthread 39 is provided to retain the half-shells 20 and 21 against one another.

In the embodiment of FIG. 8, a slight modification of the base 10, as presently used, must be made. On the other hand, in the other embodiments shown it is possible to use, with a cylindrical wall formed of four elements 20,21, 22, 23, exactly the same upper and lower closure parts as are presently used with a cylindrical wall in one piece.

Figure 4:
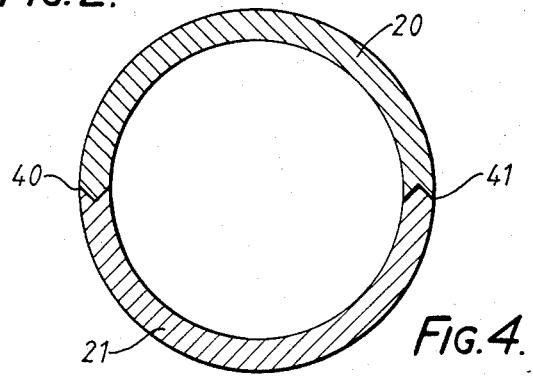
FIG. 4 is a cross-section on the line 4—4 of FIG. 3.

The two half-shells 20 and 21 interlock in their cylindrical main central portion 25, as shown in FIG. 4, along diametrically opposite connection generatrices 40, 41 of the two half-shells. The interlocking surface has as shown a V-shaped cross-section. In the two threaded portions 26 and 27 the two half-shells 20 and 21 are applied against one another on a plane surface. It would also be possible to provide a seal of tetrafluoroethylene and/or to deposit a film of plastics material on the contacting surfaces. As described above the half-shells 20,21 together define a cylinder. In a modification they may together define a frusto-cone, and have semifrustoconical inner and outer faces, the container then being generally frustoconical.

The tests carried out have shown the ease with which, after unscrewing the rings 22 and 23, the two half-shells 20 and 21 can be separated, for example by means of light blows with a wooden mallet.

It will be understood that numerous modifications can be adopted both as regards the shell elements and as regards the means of holding them against one another.

There is thus provided a container which enables evolution tests to be carried out within the consistency time of a material, without the presence of an operator after the tests have been started; the separation of the mass of hardened material from the container holding it can be effected later on when an operator is present. Even if an operator is present at the end of the test and immediately attends to the separation of the partially hardened material from the container, the invention facilitates this separation; moreover, it makes it possible for any shortcomings on the part of the operator to be remedied. Additionally, once the container has been assembled it can have exactly the same configuration as containers presently in use.

What is claimed is:

1. A consistometer for testing rheologically evolutive materials, comprising:
   (a) a housing vessel (1) defining an internal chamber (2),
   (b) a container (3) for rheologically evolutive materials removably disposed with the chamber,
   (c) agitator means (15) disposed within the container and rotatable relative thereto,
   (d) resilient means for restraining the rotation of one of the container and the agitator means,
   (e) means (18) operatively associated with the resilient means for indicating the degree of rotational restraint,
   (f) means (19) for establishing desired temperature and pressure conditions in the chamber, and
   (g) means (4–6) coupled to another one of the container and the agitator means for implementing relative rotation therebetween,
   (h) wherein the container comprises a side wall of generally cylindrical or frustoconical shape formed by two longitudinal half-shells (20, 21) separably connected to one another along two diametrically opposite connection generatrices (40, 41) and having externally threaded longitudinal end portions (26, 27), and two unitary clamp rings (22, 23) respectively screwed one on each of said threaded longitudinal end portions to clamp said two half-shells one against the other, said container thus being readily disassemblable to facilitate the removal of evolutively hardened material.

2. A consistometer according to claim 1, wherein said two half-shells have a continuous inner face (24) of semicylindrical or semifrustoconical shape and an outer face (25) comprising a semicylindrical or semifrustoconical main central portion lying between two externally threaded end portions of smaller diameter connected to said central portion outer face by chamfers (28, 29), and said clamp rings each have a frustoconical annular face (30, 34) whose inclination is complementary to that of said chamfers and which is intended to be applied against one of said chamfers on threading of said clamp rings on said half-shells.

3. A consistometer according to claim 2, wherein said half-shells interlock along said diametrically opposite connection generatrices by means of complementary longitudinal surfaces of V-shaped cross-section.

* * * * *